(12) United States Patent
Meng et al.

(10) Patent No.: US 12,349,477 B2
(45) Date of Patent: Jul. 1, 2025

(54) X-RAY DETECTOR AND METHOD FOR FORMING THE SAME

(71) Applicants: Beijing BOE Technology Development Co., Ltd., Beijing (CN); BOE Technology Group Co., Ltd., Beijing (CN)

(72) Inventors: Fanli Meng, Beijing (CN); Zeyuan Li, Beijing (CN); Jiangbo Chen, Beijing (CN); Ding Ding, Beijing (CN)

(73) Assignees: Beijing BOE Technology Development Co., Ltd., Beijing (CN); BOE Technology Group Co., Ltd., Beijing (CN)

( * ) Notice: Subject to any disclaimer, the term of this patent is extended or adjusted under 35 U.S.C. 154(b) by 0 days.

(21) Appl. No.: 17/777,422

(22) PCT Filed: May 31, 2021

(86) PCT No.: PCT/CN2021/097206
§ 371 (c)(1),
(2) Date: May 17, 2022

(87) PCT Pub. No.: WO2022/252008
PCT Pub. Date: Dec. 8, 2022

(65) Prior Publication Data
US 2024/0170505 A1    May 23, 2024

(51) Int. Cl.
*A61B 6/00*    (2024.01)
*H01L 23/31*    (2006.01)
(Continued)

(52) U.S. Cl.
CPC ....... *H10F 39/103* (2025.01); *H01L 23/3171* (2013.01); *H10D 84/856* (2025.01); *H10D 86/021* (2025.01)

(58) Field of Classification Search
CPC ..... H01L 27/144; H01L 27/092; H01L 27/12; H01L 27/1443; H01L 27/0922;
(Continued)

(56) References Cited

U.S. PATENT DOCUMENTS

| 2011/0163240 A1 | 7/2011 | Suwa et al. |
| 2017/0285185 A1 | 10/2017 | Jiang |

(Continued)

FOREIGN PATENT DOCUMENTS

| CN | 102460216 A | 5/2012 |
| CN | 103779362 A | 5/2014 |

(Continued)

*Primary Examiner* — Jurie Yun
(74) *Attorney, Agent, or Firm* — IPro, PLLC (57) ABSTRACT

The present disclosure relates to an X-RAY detector including a base substrate and a plurality of detection units arranged on the base substrate. Each detection unit includes a light conversion element and a switching transistor, the light conversion element is configured to convert an optical signal into an electrical signal, and the switching transistor is configured to output the electrical signal to a reading signal line. Each detection unit further includes a radiation shielding structure located at a light-entering side of the detection unit, and an orthogonal projection of the radiation shielding structure onto the base substrate fully covers an orthogonal projection of the switching transistor onto the base substrate. The present disclosure further relates to a method for forming the X-RAY detector.

11 Claims, 6 Drawing Sheets

(51) Int. Cl.
*H10D 84/85* (2025.01)
*H10D 86/01* (2025.01)
*H10F 39/10* (2025.01)

(58) Field of Classification Search
CPC ........... H01L 27/1259; H01L 27/14612; H01L 27/14623; H01L 27/14663; H01L 27/14692; H01L 23/31; H01L 23/3171; A61B 6/00
See application file for complete search history.

(56) References Cited

U.S. PATENT DOCUMENTS

2018/0114802 A1 4/2018 Lin
2021/0175273 A1* 6/2021 Yoon ................. H01L 27/14658

FOREIGN PATENT DOCUMENTS

| CN | 105093259 A | 11/2015 |
| CN | 105720063 A | 6/2016 |
| CN | 107623011 A | 1/2018 |
| JP | 2001099942 A | 4/2001 |

* cited by examiner

X-RAY DETECTOR AND METHOD FOR FORMING THE SAME

CROSS-REFERENCE TO RELATED APPLICATION

This application is the U.S. national phase of PCT Application No. PCT/CN2021/097206 filed on May 31, 2021, which is incorporated by reference herein in its entirety.

TECHNICAL FIELD

The present disclosure relates to the field of detector, in particular to an X-RAY detector and a method or forming the X-RAY detector.

BACKGROUND

At present, a semiconductor flat panel detector (FPD) has been widely used as an optical detection and sensing member in the field of digital medical image. In addition to sensitivity, signal-to-noise ratio and resolution (MTF), as well as detection frame rate, reliability is also required, and the most critical performance indicator of FPD is a dose of radiation tolerance. In the case of a detector, a pixel structure thereof is usually that a light conversion element and a transistor serving as a switch are arranged in each pixel. The light conversion element generates photo-charge accumulation when exposed to light, and signal charge integration (TFT off) and data reading (TFT on) are controlled through the transistor (TFT) during progressive scanning. In practice, a switching member of the transistor tend to fail when the radiation accumulates to a certain extent. Currently, there is no effective isolation between the light conversion element and the transistor. In the case that the light conversion element is exposed to radiation, there is no effective radiation shielding for a transistor control circuit.

SUMMARY

In order to address the above-mentioned technical issue, the present disclosure provides an X-RAY detector and a method for forming the X-RAY detector, so as to address the issue that the service life is adversely affected due to insufficient radiation shielding for the transistor when performing ray detection.

To achieve the above object, the technical solutions in the embodiments of the present disclosure are as follows.

An X-RAY detector is provided, including a base substrate and a plurality of detection units arranged on the base substrate. Each detection unit includes a light conversion element for converting an optical signal into an electrical signal and a switching transistor for outputting the electrical signal to a reading signal line. Each detection unit further includes a radiation shielding structure located at a light-entering side of the detection unit, and an orthogonal projection of the radiation shielding structure onto the base substrate fully covers an orthogonal projection of the switching transistor onto the base substrate.

In a possible embodiment of the present disclosure, the switching transistor and the light conversion element are respectively located at two opposite sides of the base substrate, a via hole is provided in the base substrate, and the switching transistor is coupled to the light conversion element through the via hole.

In a possible embodiment of the present disclosure, the light conversion element is located at the light-entering side of the base substrate, the switching transistor is located at a backlight side of the base substrate, and the radiation shielding structure is arranged between the light conversion element and the base substrate, or between the base substrate and the switching transistor.

In a possible embodiment of the present disclosure, the radiation shielding structure is a planar structure arranged on the base substrate in an entire layer manner, and the via hole is provided penetrating the base substrate and the radiation shielding structure.

In a possible embodiment of the present disclosure, the radiation shielding structure includes a patterning shielding layer, and the patterning shielding layer includes a light-shielding region corresponding to the switching transistor, and a light-transmitting region located outside the light-shielding region.

In a possible embodiment of the present disclosure, the light conversion element includes a first electrode, a direct conversion material layer and a second electrode laminated one on another sequentially in a direction away from the base substrate; or, the light conversion element is a PIN diode or an NIP diode or an Avalanche Photo Diode (APD).

In a possible embodiment of the present disclosure, the switching transistor and the light conversion element are located at a same side of the base substrate, the light conversion element is a photodiode, and an active layer of the switching transistor extends in a direction approaching the light conversion element and is further used as an N-type layer or a P-type layer of the light conversion element.

In a possible embodiment of the present disclosure, the switching transistor and the light conversion element are located at a same side of the base substrate, the light conversion element is a photodiode, and an active layer of the switching transistor extends to a side of the photodiode close to the base substrate in a direction approaching the light conversion element and forms a connection layer coupled to a P-type layer or an N-type layer of the photodiode.

In a possible embodiment of the present disclosure, the radiation isolation structure includes a radiation shielding layer between the switching transistor and the base substrate.

In a possible embodiment of the present disclosure, the switching transistor is of a bottom-gate structure, a top-gate structure or a Complementary Metal Oxide Semiconductor (CMOS) structure.

In a possible embodiment of the present disclosure, the light conversion element is a PIN diode or an NIP diode.

In a possible embodiment of the present disclosure, each detection unit further includes an X-RAY conversion layer arranged at the light-entering side of the detection unit, and the X-RAY conversion layer is configured to convert X rays into a visible optical signal.

A method for forming the above-mentioned X-RAY detector, including: forming a radiation shielding layer on a base substrate, and forming a light conversion element and a switching transistor at a same side or opposite sides of the base substrate respectively.

In a possible embodiment of the present disclosure, the forming the light conversion element and the switching transistor at the same side or opposite sides of the base substrate respectively, includes: forming the switching transistor at a backlight side of the base substrate, forming a via hole in the base substrate penetrating the base substrate and the radiation shielding layer, and forming the light conversion element at a side of the radiation shielding layer away from the base substrate, where the light conversion element is coupled to the switching transistor through the via hole.

In a possible embodiment of the present disclosure, prior to forming the switching transistor at the backlight side of base substrate, the method further includes: forming a first connection metal layer at the backlight side of the base substrate, where the first connection metal layer is coupled to a source electrode of the switching transistor; prior to the forming the light conversion element at the side of the radiation shielding layer away from the base substrate, the method further includes: forming a second connection metal layer at the side of the radiation shielding layer away from the base substrate, where the second connection metal layer is coupled to the first connection metal layer through the via hole.

In a possible embodiment of the present disclosure, the forming the light conversion element and the switching transistor at the same side or opposite sides of the base substrate respectively is forming the light conversion element and the switching transistor at the same side, including: forming a buffer layer on the radiation shielding layer, forming an active layer on the buffer layer, forming a gate insulating layer and a gate electrode of the switching transistor in a first region of the active layer, forming an I-type layer and a P-type layer of the light conversion element sequentially in a second region located at one side of the first region of the active layer, where the active layer is further used as an N-type layer of the light conversion element, forming an interlayer dielectric layer, forming a source electrode, a drain electrode coupled to the active layer, and a metal lead coupled to the light conversion element by using a same process, forming a passivation layer, and forming an encapsulation layer.

In a possible embodiment of the present disclosure, the forming the light conversion element and the switching transistor at the same side or opposite sides of the base substrate respectively is forming the light conversion element and the switching transistor at the same side, including: forming a buffer layer on the radiation isolation layer, forming an active layer on the buffer layer, forming a gate insulating layer and a gate electrode of the switching transistor in a first region of the active layer, forming an I-type layer and an N-type layer of the light conversion element sequentially in a second region located at one side of the first region of the active layer, wherein the active layer is further used as a P-type layer of the light conversion element, forming an interlayer dielectric layer, forming a source electrode, a drain electrode coupled to the active layer, and a metal lead coupled to the light conversion element by using a same process, forming a passivation layer, and forming an encapsulation layer.

Beneficial effects of the present disclosure are as follows. It is able to effectively provide the radiation shielding for the switching transistor through the radiation shielding structure, so as to improve the radiation-resistant performance of the detector, and prolong a service life of the detector.

DETAILED DESCRIPTION

In order to make the objects, the technical solutions and the advantages of the present disclosure more apparent, the present disclosure will be described hereinafter in a clear and complete manner in conjunction with the drawings and embodiments. Apparently, the following embodiments merely relate to a part of, rather than all of, the embodiments of the present disclosure, and based on these embodiments, a person skilled in the art may, without any creative effort, obtain the other embodiments, which also fall within the scope of the present disclosure.

In the embodiments of the present disclosure, it should be appreciated that, such words as "in the middle of", "on/above", "under/below", "left", "right", "vertical", "horizontal", "inside" and "outside" may be used to indicate directions or positions as viewed in the drawings, and they are merely used to facilitate the description in the present disclosure, rather than to indicate or imply that a device or member must be arranged or operated at a specific position. In addition, such words as "first", "second" and "third" may be merely used to differentiate different components rather than to indicate or imply any importance.

As shown in FIGS. 1 to 11, an X-RAY detector is provided in the embodiments of the present disclosure, including a base substrate 1 and a plurality of detection unit arranged on the base substrate 1. Each detection unit includes a light conversion element 2 for converting an optical signal into an electrical signal and a switching transistor 3 for outputting the electrical signal to a reading signal line. Each detection unit further includes a radiation shielding structure 4 located at a light-entering side of the detection unit, and an orthogonal projection of the radiation shielding structure 4 onto the base substrate 1 fully covers an orthogonal projection of the switching transistor 3 onto the base substrate 1.

It is able to effectively provide the radiation shielding for the switching transistor through the radiation shielding structure, so as to improve the radiation-resistant performance of the detector, and prolong a service life of the detector.

The switching transistor 3 and the light conversion element 2 may be arranged at two opposite sides of the base substrate 1, as shown in FIGS. 1 to 7. The switching transistor 3 and the light conversion element 2 may also be located at a same side of the base substrate 1, as shown in FIGS. 8-11. Regardless of the arrangement, it is able to effectively provide the radiation shielding for the switching transistor through the radiation shielding structure 4.

As shown in FIGS. 1 to 7, for example, the switching transistor 3 and the light conversion element 2 are located at two opposite sides of the base substrate 1 respectively, a via hole is provided in the base substrate 1, and the switching transistor 3 is coupled to the light conversion element 2 through the via hole.

As shown in FIGS. 1 to 7, the switching transistor 3 and the light conversion element 2 are located at two opposite sides of the base substrate 1 respectively, the via hole is formed in the base substrate 1, and a conductive metal material is filled in the via hole, so as to achieve electrical connection between the switching transistor 3 and the light conversion element 2 located at two opposite sides of the base substrate 1 respectively through the metal material in the via hole. The switching transistor 3 and the light conversion element 2 are located at two opposite sides of the base substrate 1 respectively, and the radiation shielding structure 4 is arranged, so as to provide the radiation shielding for the switching transistor 3.

It should be appreciated that the via hole may be formed through a Through Glass Via (TGV) technology or a through-silicon via (TSV) technology. Since the base substrate 1 may be made of different specific materials, the process of forming the via hole may be determined according to actual needs. For example, in FIGS. 1-4 and 6, the base substrate 1 is a glass substrate and the via hole is a TGV via hole, and in FIGS. 5 and 7, the base substrate 1 is made of single crystal silicon and the via hole is a TSV via hole.

Illustratively, the light conversion element 2 is located at the light-entering side of the base substrate 1, the switching transistor 3 is located at the backlight side of the base substrate 1, and the radiation shielding structure 4 is arranged between the light conversion element 2 and the base substrate 1, or between the base substrate 1 and the switching transistor 3. In FIGS. 1 to 7, the radiation shielding structure 4 is arranged between the light conversion element 2 and the base substrate 1, which will not be particularly defined herein.

Illustratively, the radiation shielding structure 4 is a planar structure arranged on the base substrate 1 in an entire layer manner, and the via hole is arranged penetrating the base substrate 1 and the radiation shielding structure 4, as shown in FIGS. 1 to 7.

Figure 12:
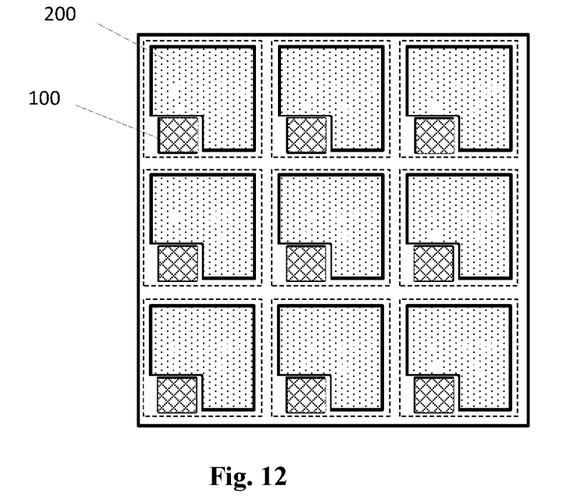
FIG. 12 is schematic view showing a patterning shielding layer according to one embodiment of the present disclosure.

As shown in FIG. 12, illustratively, the radiation shielding structure 4 includes a patterning shielding layer, and the patterning shielding layer includes a light-shielding region 100 corresponding to the switching transistor 3, and a light-transmitting region 200 located outside the light-shielding region 100.

In FIG. 12, a part including dots denotes a plurality of pixel regions, the light-shielding region 100 of the patterning shielding layer corresponds to the switching transistor 3, so as to effectively provide shielding for the switching transistor 3. The light-transmitting region 200 of the patterning isolation layer corresponds to components other than the switching transistor 3, so as to save costs.

In the embodiment of the present disclosure, in the detector shown in FIGS. 1 to 7, the light conversion element includes a first electrode, a direct conversion material layer and a second electrode laminated one on another sequentially in a direction away from the base substrate. Alternatively, the light conversion element is a PIN diode or an NIP diode or an Avalanche Photo Diode (APD).

The X-RAY detector includes a direct detector and an indirect detector. The indirect detector further includes a silicon-based detector and a glass-based detector, where the former is based on silicon-based semiconductor process (single crystal silicon Complementary Metal Oxide Semiconductor (CMOS) process), so as to form a control circuit and the light conversion element, and the glass-based detector is mainly based on Thin film transistor-liquid crystal display (TFT-LCD) display process (including amorphous silicon, oxide and Low Temperature Poly-silicon (LTPS)), so as to form a TFT control circuit and the light conversion element. In the indirect detector structure, the light conversion element may be a PIN diode or an NIP diode or an APD.

The light conversion element 2 includes a transparent electrode arranged away from the base substrate 1, so as to collect X rays. The transparent electrode may be, but not limited to, an indium tin oxide (ITO) electrode.

It should be appreciated that, in a specific embodiment of the present disclosure, the X-RAY detector is a direct detector, and the light conversion element includes a first electrode, a direct conversion material layer and a second electrode laminated one on another sequentially in a direction away from the base substrate. At this time, an electrode at a side of the light conversion element away from the base substrate may be a non-transparent metal electrode, and an X-RAY conversion layer may be omitted. In a specific embodiment of the present disclosure, the radiation shielding structure may be arranged only in the region corresponding to the switching transistor 3, so as to simplify a structure, as shown in FIGS. 8 to 11.

As shown in FIGS. 8 to 11, illustratively, the switching transistor 3 and the light conversion element 2 are located at the same side of the base substrate 1, and an active layer 10 of the switching transistor 3 in a direction approaching the light conversion element 2 and is further used as an N-type layer or a P-type layer of the light conversion element 2.

Illustratively, the radiation shielding structure 4 includes a radiation shielding layer between the switching transistor 3 and the base substrate 1.

The switching transistor 3 and the light conversion element 2 are located at the same side of the base substrate 1, and in order to effectively provide shielding for the switching transistor and ensure that the collection of rays by the light conversion element 2 is not adversely affected, the radiation shielding layer is only arranged between the switching transistor 3 and the base substrate 1.

Illustratively, the switching transistor 3 is of a bottom-gate structure, top-gate structure or CMOS structure.

Figure 1:
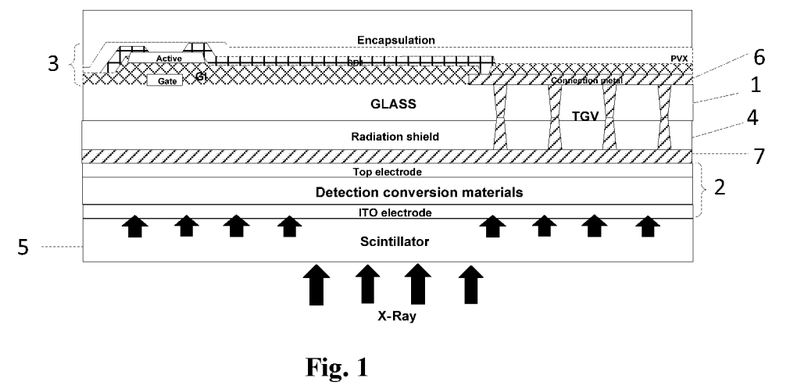
FIG. 1 is a schematic view showing an X-RAY detector according to one embodiment of the present disclosure.
Figure 2:
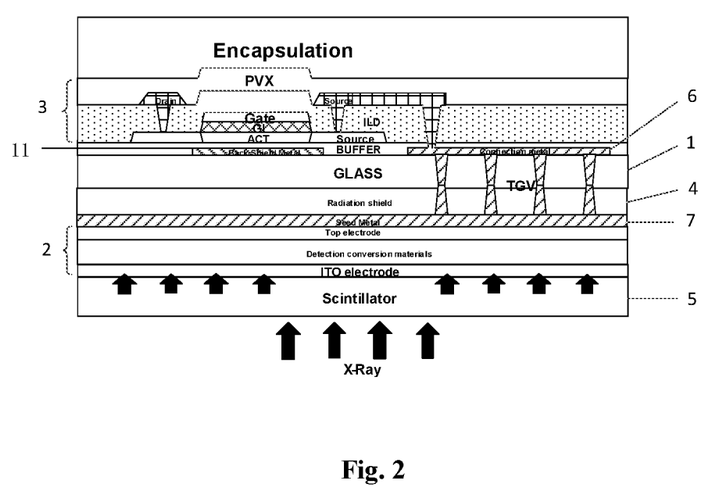
FIG. 2 is another schematic view showing the X-RAY detector according to one embodiment of the present disclosure.
Figure 3:
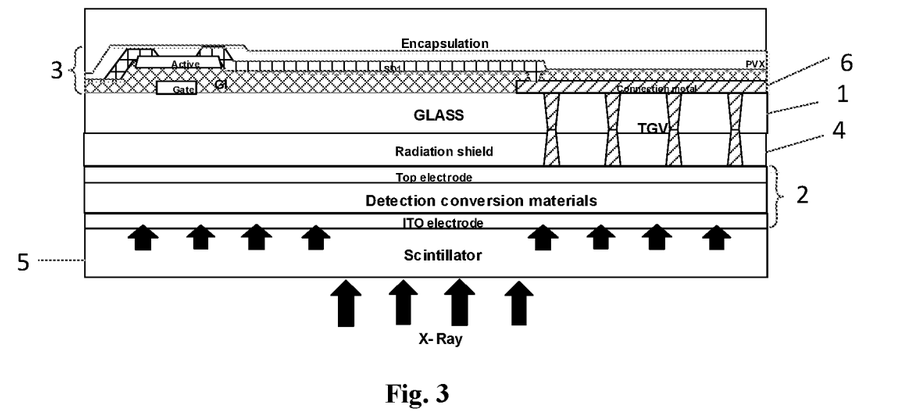
FIG. 3 is yet another schematic view showing the X-RAY detector according to one embodiment of the present disclosure.
Figure 5:
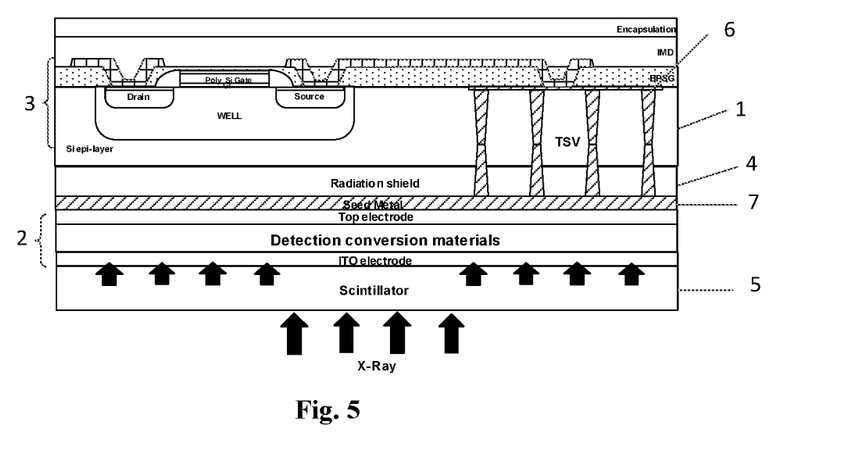
FIG. 5 is still yet another schematic view showing the X-RAY detector according to one embodiment of the present disclosure.
Figure 6:
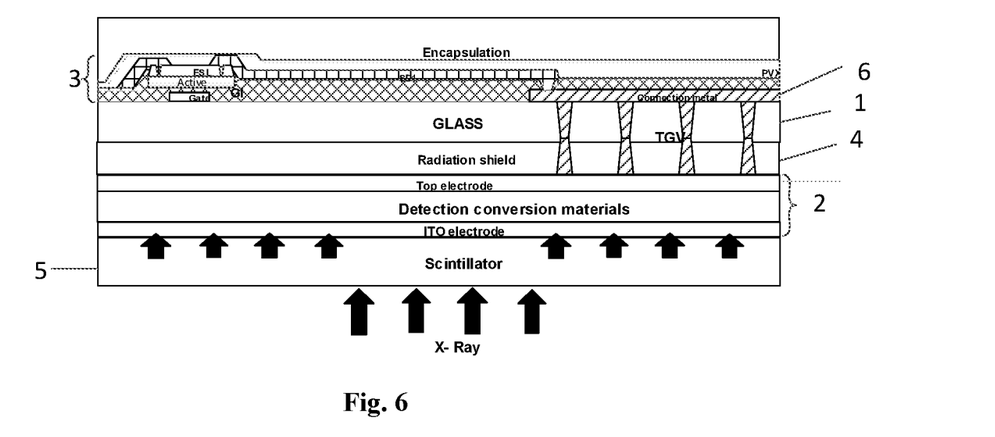
FIG. 6 is still yet another schematic view showing the X-RAY detector according to one embodiment of the present disclosure.
Figure 7:
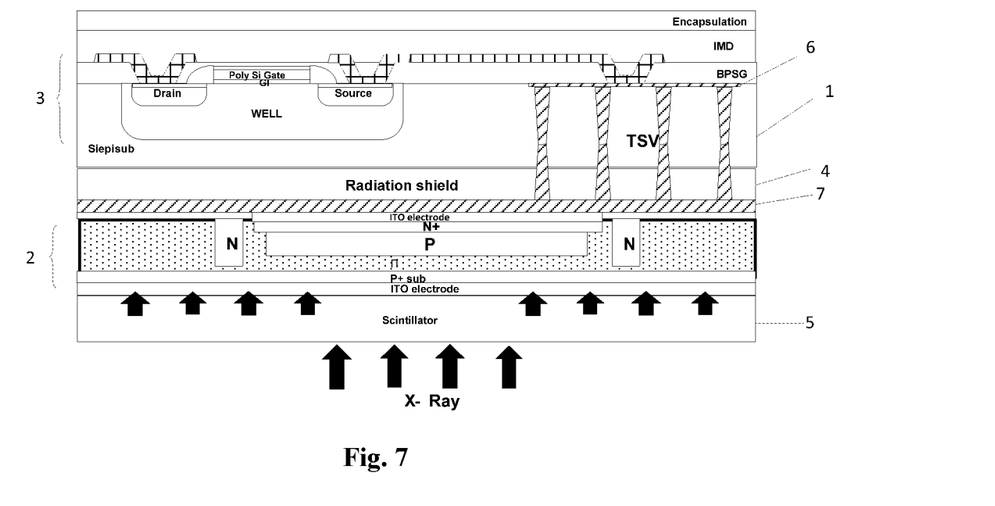
FIG. 7 is still yet another schematic view showing the X-RAY detector according to one embodiment of the present disclosure.

In FIGS. 1 and 3, the switching transistor is of a bottom-gate structure. In FIGS. 2, 4 and 8-11, the switching transistor 3 is of a top-gate structure. In FIGS. 5 and 7, the switching transistor is of a CMOS structure. In FIG. 6, the switching transistor is of an ESL structure where an etch stop layer (ESL) disposed on an active layer.

Illustratively, the light conversion element 2 is a PIN diode or an NIP diode.

Illustratively, each detection unit further includes an X-RAY conversion layer 5 disposed at the light-entering side of the detection unit, and the X-RAY conversion layer 5 is configured to convert X rays into a visible optical signal.

Figure 8:
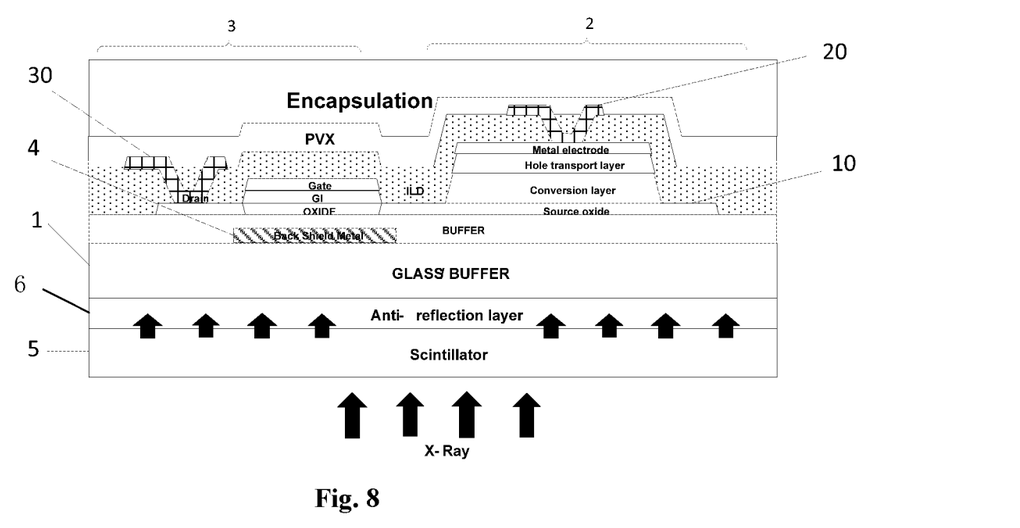
FIG. 8 is still yet another schematic view showing the X-RAY detector according to one embodiment of the present disclosure.
Figure 9:
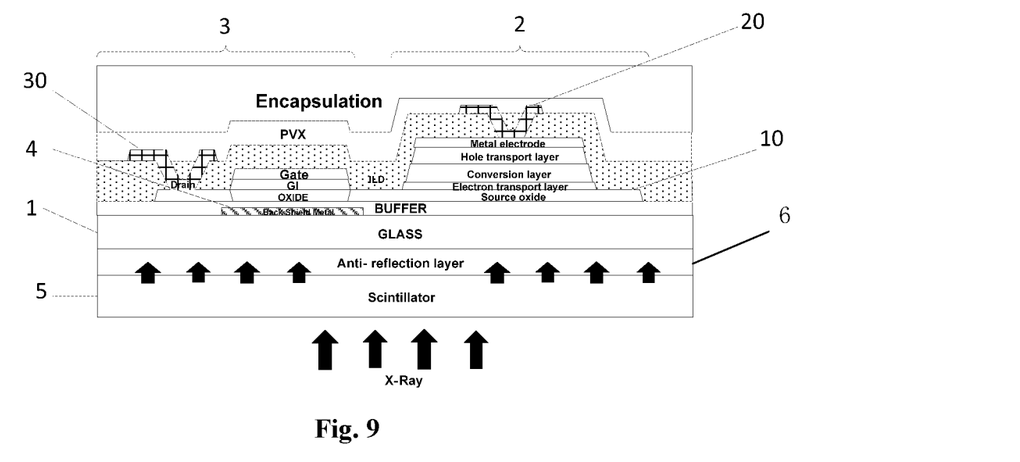
FIG. 9 is still yet another schematic view showing the X-RAY detector according to one embodiment of the present disclosure.
Figure 10:
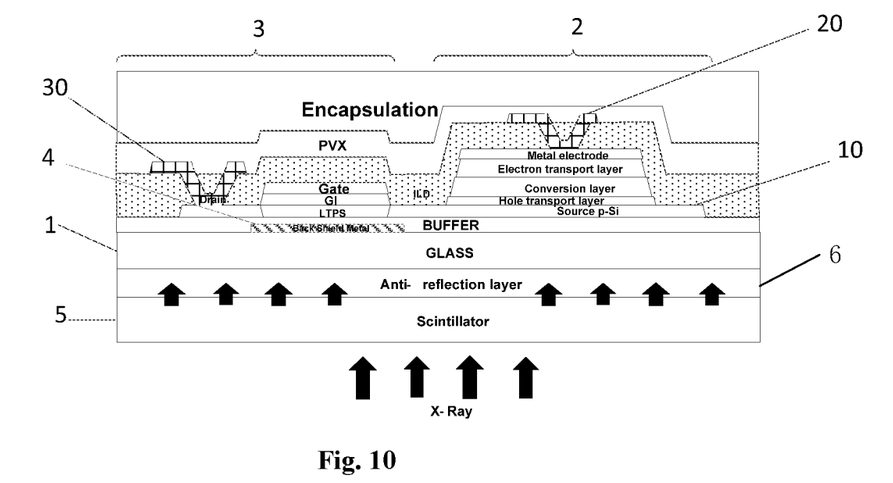
FIG. 10 is still yet another schematic view showing the X-RAY detector according to one embodiment of the present disclosure.

Illustratively, each detection unit further includes an anti-reflection layer 6 disposed between the X-RAY conversion layer 5 and the base substrate 1, so as to improve ray detection efficiency, as shown in FIGS. 8 to 10.

Referring to FIGS. 1 and 2, in the embodiment of the present disclosure, a seed metal layer 7 is provided at a side of the radiation shielding structure 4 away from the base substrate 1, a first connection metal layer 6 used to be coupled to a source electrode of the switching transistor is provided at a side of the base substrate 1 where the switching transistor 3 is arranged, and the electrical connection between the light conversion element 2 and the switching transistor 3 is achieved through a via hole between the first connection metal layer 6 and the seed metal layer 7.

In the embodiment of the present disclosure, a conductive metal material is filled in the via hole by using an electroplating process, so as to achieve the electrical connection between the light conversion element 2 and the switching transistor 3, and the seed metal layer 7 is arranged, thereby to facilitates the electroplating process.

In a process of forming the detector in FIGS. 1 and 2, after forming the radiation shielding structure 4 and the seed metal layer 7 at one side of the base substrate 1, such procedures as hole-forming and electroplating are performed at the other side of the base substrate 1, and then the first connection metal layer 6 is formed. In the detector in FIGS. 3 and 4, the seed metal layer 7 is omitted, accordingly, steps of the process are changed. The first connection metal layer 6 is formed at one side of the base substrate 1, the radiation shielding structure 4 is formed at the other side of the base substrate 1, and then such procedures as hole-forming and electroplating are performed at the other side of the base substrate 1. In other words, while functioning as a connection to the switching transistor 3, the first connection metal layer 6 is further used as a seed metal layer, so as to facilitate the electroplating process.

Figure 11:
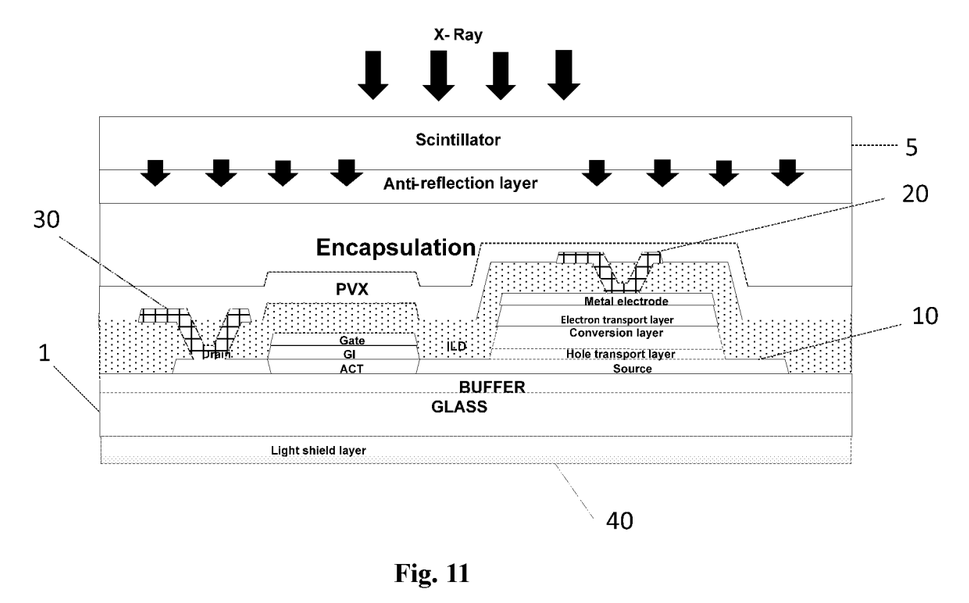
FIG. 11 is still yet another schematic view showing the X-RAY detector according to one embodiment of the present disclosure.

Referring to FIG. 11, X rays enter the base substrate 1 from the front side of the base substrate 1, the switching transistor is a p-type LTPS transistor or an N-type oxide transistor. The corresponding light conversion element is of an NIP type or a PIN type in an N-type LTPS transistor, where an I-type layer material below is directly coupled to an active layer of the transistor. A light shielding layer 40 is arranged at the back side of the base substrate 1. Since the X rays enter the base substrate 1 from a side of the active layer away from the base substrate, a radiation shielding structure does not need not be arranged at the side of the active layer close to the base substrate separately, and a multilayer structure at the side of the active layer away from the base substrate is further used as the radiation shielding structure. The light shielding layer 40 is made of a black material.

In a specific embodiment of the present disclosure, as shown in FIG. 1, the X-RAY detector includes the base substrate 1 and the plurality of detection units arranged on the base substrate 1, and each detection unit includes the light conversion element 2, the switching transistor 3 and the radiation shielding structure 4 arranged in an entire layer manner as a radiation shielding layer.

The light conversion element 2 is located at the light-entering side of the base substrate, the switching transistor 3 is located at the light-exiting side of the base substrate, and the radiation shielding structure is located between the base substrate 1 and the light conversion element 2.

The switching transistor 3 is of a bottom-gate structure, including a gate electrode, a gate insulating layer, an active layer, and a source electrode and a drain electrode coupled to the active layer laminated one on another sequentially in a direction away from the base substrate 1.

The first connection metal layer 6 is further provided at one side of the base substrate 1 close to the switching transistor 3 and arranged at a same layer as the gate electrode, and the first connection metal layer 6 is electrically connected to the source electrode through a via hole provided in the gate insulating layer.

The seed metal layer 7 is provided between the radiation shielding structure 4 and the light conversion element 2, and a via hole penetrating the base substrate 1 and the radiation shielding structure 4 is formed in the base substrate 1 through a TGV process, so as to achieve the electrical connection between the seed metal layer 7 and the first connection metal layer 6, thereby to achieve the electrical connection between the switching transistor 3 and the light conversion element 2.

A passivation (PVX) layer and an encapsulation layer are arranged sequentially at the side of the switching transistor 3 away from the base substrate 1 in the direction away from the base substrate 1.

It should be appreciated that, if the X-RAY detector is a direct type detector, the light conversion element 2 includes a first electrode, a direct conversion material layer and a second electrode laminated one on another sequentially in the direction away from the base substrate 1. In other words, it is able for the light conversion element 2 to directly convert X rays into an electrical signal.

If the X-RAY detector is an indirect-type detector, and the light conversion element 2 is a PIN diode or an NIP diode, an X-RAY conversion layer 5 is further provided at the side of the light conversion element 2 away from the base substrate 1, and the X-RAY conversion layer 5 is configured to convert X rays into a visible optical signal. In other words, the X-RAY conversion layer 5 is required to convert the X rays into a visible optical signal, so that it is able for the light conversion element 2 to convert the visible optical signal into an electrical signal.

The X-RAY detector in FIG. 2 differs from the X-RAY detector in FIG. 1 in that the switching transistor 3 has a different structure in FIG. 2. The switching transistor 3 is of a top-gate structure. Specifically, the switching transistor 3 includes an active layer, a gate insulating layer, a gate electrode, an interlayer dielectric layer, and a source electrode and a drain electrode coupled to the active layer laminated one on another sequentially in a direction away from the base substrate 1.

In the X-RAY detector shown in FIG. 2, a metal shielding layer 11 is added between the switching transistor 3 and the base substrate 1, the metal shielding layer 11 is arranged at a same layer as the first connection metal layer 6, a buffer layer is formed on the metal shielding layer 11 and the first connection metal layer 6, and the switching transistor 3 is formed on the buffer layer.

The X-RAY detector in FIG. 3 differs from the X-RAY detector in FIG. 1 in that the seed metal layer 7 is not provided in FIG. 3. In other words, the X-RAY detector in FIG. 3 and the X-RAY detector in FIG. 1 are formed through different procedure steps.

In the process of forming the detector in FIG. 1, after forming the radiation shielding structure 4 and the seed metal layer 7 at one side of the base substrate 1, such procedures as hole-forming and electroplating are performed at the other side of the base substrate 1, and then the first connection metal layer 6 is formed. In the detector in FIG. 3, the seed metal layer 7 is omitted, accordingly, steps of the process are changed. The first connection metal layer 6 is formed at one side of the base substrate 1, the radiation shielding structure 4 is formed at the other side of the base substrate 1, and then such procedures as hole-forming and electroplating are performed at the other side of the base substrate 1. In other words, while functioning as a connection to the switching transistor 3, the first connection metal layer 6 is further used as a seed metal layer, so as to facilitate the electroplating process.

Figure 4:
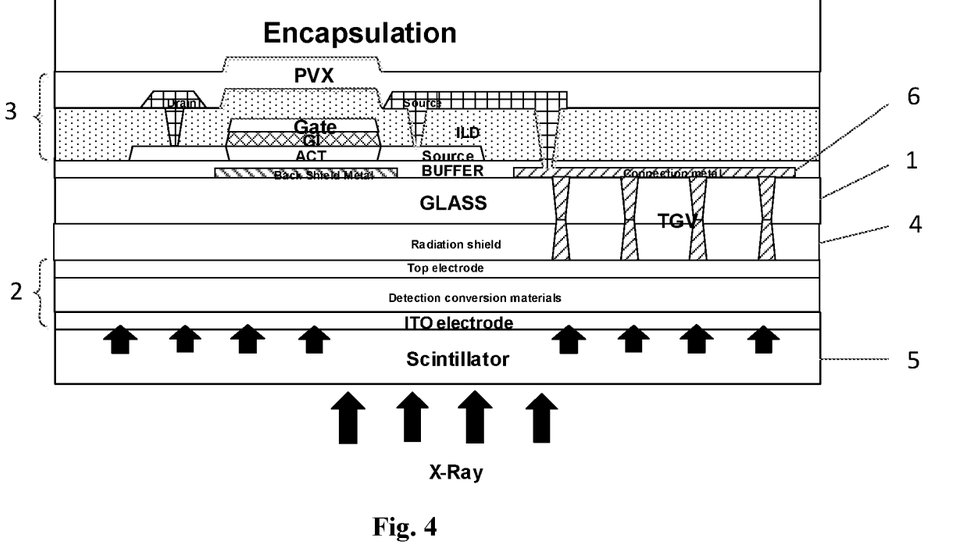
FIG. 4 is still yet another schematic view showing the X-RAY detector according to one embodiment of the present disclosure.

The X-RAY detector in FIG. 4 differs from the X-RAY detector in FIG. 2 in that the seed metal layer 7 is not provided in FIG. 4.

The X-RAY detector in FIG. 5 differs from the X-RAY detector in FIG. 1 in that the base substrate 1 in FIG. 1 is made of glass, and the base substrate 1 in FIG. 5 is made of monocrystalline silicon. The via hole in FIG. 5 is a TSV via hole. The switching transistor 3 is a metal oxide semiconductor field effect transistor (MOSFET) formed by using a CMOS process, and includes an active region formed on the base substrate 1, a drain electrode region and a source electrode region located at two sides of the active region respectively, and a gate insulating layer formed on the active region, a gate electrode formed on the gate insulating layer, a dielectric layer formed on the gate electrode, a source electrode and a drain electrode formed on the dielectric layer, the source electrode is coupled to the drain electrode region through a via hole and the source electrode is coupled to the source electrode region through a via hole.

The X-RAY detector in FIG. 6 differs from the X-RAY detector in FIG. 1 in that the switching transistor 3 is an ESL structure in FIG. 6, i.e., an etched stop layer (ESL) is formed on the active layer.

The X-RAY detector in FIG. 7 differs from the detector in FIG. 5 in that the light conversion element is an APD (e.g., a silicon-based pinned diode, an avalanche diode). In FIG. 7, the APD includes a bottom electrode, a P+ substrate, an intrinsic layer formed on the P+ substrate, a P-type layer, an N+ contact layer and a top electrode laminated one on another and formed by using an ion doping process in a direction away from the P+ substrate, and an N-type layer formed at two sides of the P-type layer.

In the X-RAY detector shown in FIGS. 1 to 7, the switching transistor 3 and the light conversion element 2 are located at the opposite sides of the base substrate 1, and in the X-RAY detector shown in FIGS. 8 to 11, the switching transistor 3 and the light conversion element 2 are located at the same side of the base substrate 1, and the light conversion element 2 is a PIN diode. Specifically, referring to FIG. 8, the radiation shielding structure 4 is formed on the base substrate 1, and the radiation shielding structure 4 is only arranged between the switching transistor 3 and the base substrate 1. A buffer layer is formed on the radiation shielding structure 4, an active layer 10 is formed on the buffer layer, and the active layer extends at one side to form an N-type layer of the light conversion element. A gate insulating layer and a gate electrode of the switching transistor 3 are formed on an upper left portion of the active layer 10, and an I-type layer, a P-type layer and a top electrode of the light conversion element are formed on an upper right portion of the active layer. An interlayer dielectric (ILD) layer is formed on the gate electrode and the top electrode, a drain electrode coupled to the active layer through a via hole and a metal lead 20 coupled to the top electrode are formed on the interlayer dielectric layer ILD, a passivation (PVX) layer is formed on the ILD layer, and an encapsulation layer is formed on the passivation (PVX) layer.

An anti-reflection layer 6 and an X-RAY conversion layer 5 are laminated one on another at one side of the base substrate 1 away from the switching transistor 3 in the direction away from the base substrate 1.

Based on the above scheme, photo-generated carriers of the PIN diode are directly transmitted to the drain electrode of the switching transistor 3 through an N-type layer which the active layer of the switching transistor 3 is further used as, as compared with a conventional structure where a bottom electrode of a PIN diode is coupled to a source electrode of a switching transistor through a connection metal, it is able to shorten a transmission path, simplify the structure and reduce process steps.

The X-RAY detector in FIG. 9 differs from the X-RAY detector in FIG. 8 in that an electron transport layer is added between the I-layer of the PIN diode and the active layer in FIG. 9. In this case, the electron transport layer is an N-type transmission layer, and the part that the active layer extends to the PIN diode and coupled to the N-type transmission layer is an N-type oxide layer, and photo-generated carriers of the PIN diode may enter the N-type oxide layer (i.e., the active layer 10) via the N-type transmission layer, so as to simplify the structure.

The X-RAY detector in FIG. 10 differs from the X-RAY detector in FIG. 9 in that the switching transistor in FIG. 9 is an oxide semiconductor transistor, and the switching transistor in FIG. 10 is a P-type LTPS transistor. The light conversion element in FIG. 9 is a PIN diode, the light conversion element in FIG. 10 is an NIP diode, and the NIP diode in FIG. 10 includes a top electrode, an N-type layer (i.e., an electron transport layer), an I-type layer (i.e., a conversion layer) and a P-type layer (i.e., a hole transport layer) laminated one on another, where the P-type layer is coupled to the active layer 10 (e.g., a P-type polycrystalline silicon layer), and photo-generated carriers of the NIP diode may enter the active layer 10 through the P-type layer and then transfer to the drain electrode of the switching transistor 3.

The X-RAY detector in FIG. 11 differs from the X-RAY detector in FIG. 10 in that X rays enter from the front side. In other words, both the switching transistor 3 and the light conversion element 2 are located at the light-entering side of the base substrate 1, and a light shielding layer 40 is provided at the back side of the base substrate 1. Since the X rays enter the base substrate 1 from a side of the active layer away from the base substrate, a radiation shielding structure does not need not be arranged at the side of the active layer close to the base substrate separately, and a multilayer structure at the side of the active layer away from the base substrate is further used as the radiation shielding structure.

The light shielding layer 40 is made of a black material.

A method for forming the above-mentioned X-RAY detector is further provided in the embodiment of the present disclosure, including: forming a radiation shielding layer on the base substrate 1, and forming the light conversion element 2 and the switching transistor 3 at the same side or opposite sides of base substrate 1, respectively.

Referring to FIGS. 1 to 7, illustratively, the forming the light conversion element 2 and the switching transistor 3 at the same side or opposite sides of the base substrate 1 respectively, includes: forming the switching transistor 3 at a backlight side of the base substrate 1, forming a via hole in the base substrate 1 penetrating the base substrate 1 and the radiation shielding layer, and forming the light conversion element 2 at a side of the radiation shielding layer away from the base substrate, where the light conversion element 2 is coupled to the switching transistor 3 through the via hole.

Illustratively, prior to forming the switching transistor 3 at the backlight side of base substrate 1, the method further includes: forming a first connection metal layer 6 at the backlight side of the base substrate 1, where the first connection metal layer 6 is coupled to a source electrode of the switching transistor 3; prior to the forming the light conversion element 2 at the side of the radiation shielding layer away from the base substrate 1, the method further includes: forming a second connection metal layer (i.e., the seed metal layer 7) at the side of the radiation shielding layer away from the base substrate 1, where the second connection metal layer is coupled to the first connection metal layer 6 through the via hole.

Referring to FIGS. 8 to 11, illustratively, the forming the light conversion element 2 and the switching transistor 3 at the same side or opposite sides of the base substrate respectively is forming the light conversion element and the switching transistor at the same side, which specifically includes: forming a buffer layer on the radiation shielding layer, forming an active layer 10 on the buffer layer, forming a gate insulating (GI) layer and a gate electrode (Gate) of the switching transistor 3 in a first region of the active layer 10, forming an I-type layer and a P-type layer of the light conversion element 2 sequentially in a second region located at one side of the first region of the active layer 10, where the active layer 10 is further used as an N-type layer of the light conversion element 2, forming an interlayer dielectric (ILD) layer, forming a drain electrode 30 coupled to the active layer 10, and a metal lead 20 coupled to the light conversion element 2 by using a same process, forming a passivation (PVX) layer, and forming an encapsulation layer.

Illustratively, the forming the light conversion element 2 and the switching transistor 3 at the same side or opposite sides of the base substrate 1 respectively is forming the light conversion element and the switching transistor at the same side, which specifically includes: forming a buffer layer on the radiation isolation layer, forming an active layer 10 on the buffer layer (the buffer layer Buffer functions to isolate the active layer 10 from the base substrate 1), forming a gate insulating (GI) layer and a gate electrode of the switching transistor 3 in a first region of the active layer 10, forming an I-type layer and an N-type layer of the light conversion element sequentially in a second region located at one side of the first region of the active layer 10, where the active layer is further used as a P-type layer of the light conversion element, forming an interlayer dielectric (ILD) layer, forming a drain electrode coupled to the active layer, and a metal lead 20 coupled to the light conversion element 2 by using a same process, forming a passivation (PVX) layer, and forming an encapsulation layer.

A conventional light conversion element includes a first electrode, a second electrode, and a P-type layer, an I-type layer and an N-type layer located between a top electrode and a bottom electrode, and the switching transistor includes an active layer, a gate insulating layer and a gate electrode, an interlayer dielectric layer, a source-to-drain electrode metal layer coupled to the active layer through a via hole, the first electrode of the light conversion element is coupled to a source electrode of the switching transistor. As compared with the conventional structure, in the embodiments of the present disclosure, the active layer 10 of the switching transistor 3 is further used as the N-type layer or the P-type layer of the light conversion element 2, and the source electrode and the metal lead that is between the light conversion element and the switching transistor are omitted, electrons generated through exciting an organic conversion layer (i.e., the I-type layer) of the light conversion element by using light may be directly enter the active layer, so as to avoid the energy loss due to an excessively long transmission path, and reduce the processing procedures of the device.

In the embodiments of the present disclosure, a channel region of the active layer may be of an ACT structure or made of an oxide (e.g., a semiconductor oxide), and when the channel region of the active layer is of the ACT structure, it may be made of indium gallium zinc oxide (IGZO), indium tin zinc oxide (ITZO), IGZXO, ITZXO, etc.

In the embodiments of the present disclosure, the gate insulating (GI) layer may be made of $SiO_2/SiN_x$ or hydrogen-free $SiN_x$:F.

In the embodiments of the present disclosure, the gate electrode may be made of a single metal layer of Mo, Ti, Al or Nd, or a lamination metal layer of Mo/AlNd/Mo, Ti/Al/Ti or MTD/Cu/MTD.

In a PIN-type light conversion element, the P-type layer may be made of an organic material such as P3HT, PTAA, spiro-OMeTAD or an inorganic material such as $MoO_3$, NiO, $Cu_2O$, the I-type layer may be made of various photosensitive organic polymers or perovskite (e.g., perovskite material with an AaBbXx molecular structure, where Aa includes any one or more of organic amine group, formamidine, cesium ion, rubidium ion, silver ion and cuprous ion, Bb includes lead ion or bismuth ion, Xx includes any one or more of iodine, chlorine and bromine), and the N-type layer is formed by the active layer made of oxide extending at one end in a large area.

In the embodiments of the present disclosure, each electrode of the light conversion element may be made of Ag, Au or Al.

In the embodiments of the present disclosure, the interlayer dielectric (ILD) layer may be made of $SiO_2$ or hydrogen-free $SiN_x$:F.

In the embodiments of the present disclosure, the drain electrode in the switching transistor (or the metal lead 20 of the light conversion element) may be made of a single metal layer of Mo, Ti, Al, or Nd, or a lamination metal layer of Mo/AlNd/Mo, Ti/Al/Ti, or MTD/Cu/MTD.

In the embodiments of the present disclosure, the passivation (PVX) layer is made of $SiO_2$ or hydrogen-free $SiN_x$:F.

In the embodiments of the present disclosure, the encapsulation layer is of a multi-layer structure formed by an inorganic film layer (e.g., made of $SiO_2$ or hydrogen-free $SiN_x$:F) and an organic film layer (e.g., made of resin, etc.).

Referring to FIG. 10, in the embodiment of the present disclosure, the switching transistor is a p-type LTPS, the light conversion element is an NIP diode, the N-type layer of the NIP diode is made of C60 (and derivatives thereof), PCBM (and derivatives thereof), etc., and the P-type layer of the NIP diode is made of PEDOT: PSS cuprous thiocyanate (CuSCN), cuprous iodide (Cue, Poly-TPD, PCDTBT, Tributyl phosphate (TBP), etc.

The above embodiments are optional embodiments of the present disclosure, it should be appreciated that, those skilled in the art may make various improvements and modifications without departing from the principle of the present disclosure, and theses improvement and modifications shall fall within the protection scope of the present disclosure.

What is claimed is:

1. An X-RAY detector, comprising a base substrate and a plurality of detection units arranged on the base substrate, wherein each detection unit comprises a light conversion element for converting an optical signal into an electrical signal and a switching transistor for outputting the electrical signal to a reading signal line, wherein each detection unit further comprises a radiation shielding structure located at a light-entering side of the detection unit, and an orthogonal projection of the radiation shielding structure onto a plane where the base substrate is located fully covers an orthogonal projection of the switching transistor onto the plane where the base substrate is located; wherein the plane where the base substrate is located is perpendicular to a direction from the light-entering side of the base substrate to a light-exiting side of the base substrate;
wherein the switching transistor and the light conversion element are located at two opposite sides of the base substrate respectively, a via hole is provided in the base substrate, and the switching transistor is coupled to the light conversion element through the via hole.

2. The X-RAY detector according to claim 1, wherein the light conversion element is located at the light-entering side of the base substrate, the switching transistor is located at the light-exiting side of the base substrate, and the radiation shielding structure is arranged between the light conversion element and the base substrate, or between the base substrate and the switching transistor.

3. The X-RAY detector according to claim 2, wherein the radiation shielding structure is a planar structure arranged on the base substrate in an entire layer manner, and the via hole is provided penetrating the base substrate and the radiation shielding structure.

4. The X-RAY detector according to claim 2, wherein the radiation shielding structure comprises a patterning shielding layer, and the patterning shielding layer comprises a light-shielding region corresponding to the switching transistor, and a light-transmitting region located outside the light-shielding region.

5. The X-RAY detector according to claim 1, wherein the light conversion element comprises a first electrode, a direct conversion material layer and a second electrode laminated one on another sequentially in a direction away from the base substrate;
or, the light conversion element is a PIN diode or an NIP diode or an Avalanche Photo Diode (APD).

6. The X-RAY detector according to claim 1, wherein the light conversion element is a PIN diode or an NIP diode.

7. The X-RAY detector according to claim 1, wherein the switching transistor is of a bottom-gate structure, a top-gate structure or a Complementary Metal Oxide Semiconductor (CMOS) structure.

8. The X-RAY detector according to claim 1, wherein each detection unit further comprises an X-RAY conversion layer arranged at the light-entering side of the detection unit, and the X-RAY conversion layer is configured to convert X rays into a visible optical signal.

9. A method for forming the X-RAY detector according to claim 1, comprising:
forming a radiation shielding layer on a base substrate; and
forming a light conversion element and a switching transistor at opposite sides of the base substrate respectively;
wherein the forming the light conversion element and the switching transistor at opposite sides of the base substrate respectively, comprises:
forming the switching transistor at a light-exiting side of the base substrate;
forming a via hole in the base substrate penetrating the base substrate and the radiation shielding layer; and
forming the light conversion element at a side of the radiation shielding layer away from the base substrate, wherein the light conversion element is coupled to the switching transistor through the via hole.

10. The method according to claim 9, wherein prior to forming the switching transistor at the light-exiting side of base substrate, the method further comprises:
forming a first connection metal layer at the light-exiting side of the base substrate, wherein the first connection metal layer is coupled to a source electrode of the switching transistor;
prior to the forming the light conversion element at the side of the radiation shielding layer away from the base substrate, the method further comprises:
forming a second connection metal layer at the side of the radiation shielding layer away from the base substrate, wherein the second connection metal layer is coupled to the first connection metal layer through the via hole.

11. The X-RAY detector according to claim 1, wherein the switching transistor is of a bottom-gate structure, a top-gate structure or a Complementary Metal Oxide Semiconductor (CMOS) structure.

* * * * *